United States Patent
Moeller et al.

(10) Patent No.: US 8,076,442 B2
(45) Date of Patent: Dec. 13, 2011

(54) POLYAMINO AND/OR POLYAMMONIUM/POLYSILOXANE COPOLYMER COMPOUNDS WITH POLYALKYLENE OXIDE UNITS IN COMB-SHAPED ARRANGEMENT

(75) Inventors: Annette Moeller, Leverkusen (DE); Christopher Roos, Cologne (DE); Roland Wagner, Siegburg (DE); Karl-Heinz Sockel, Leverkusen (DE); Karl-Heinz Stachulla, Leverkusen (DE); Anita Witossek, Langenfeld (DE); Horst Lange, Boghum (DE)

(73) Assignee: Momentive Performance Materials GmbH, Leverkusen (DE)

( * ) Notice: Subject to any disclaimer, the term of this patent is extended or adjusted under 35 U.S.C. 154(b) by 508 days.

(21) Appl. No.: 11/909,723

(22) PCT Filed: Mar. 30, 2006

(86) PCT No.: PCT/EP2006/002910
§ 371 (c)(1),
(2), (4) Date: Jan. 11, 2008

(87) PCT Pub. No.: WO2006/103075
PCT Pub. Date: Oct. 5, 2006

(65) Prior Publication Data
US 2008/0213208 A1 Sep. 4, 2008

(30) Foreign Application Priority Data
Mar. 30, 2005 (DE) .................. 10 2005 014 311

(51) Int. Cl.
*C08G 77/26* (2006.01)
(52) U.S. Cl. .............. 528/28; 528/27; 528/29; 528/38
(58) Field of Classification Search ............... 528/28, 528/38, 27, 29
See application file for complete search history.

(56) References Cited

U.S. PATENT DOCUMENTS

| 3,560,543 A | 2/1971 | Plueddemann et al. |
| 2006/0235181 A1 * | 10/2006 | Lange et al. .................. 528/28 |

FOREIGN PATENT DOCUMENTS

| DE | 10214290 A1 | | 10/2003 |
| WO | 02/10254 A1 | | 2/2002 |
| WO | 02/10257 A1 | | 2/2002 |
| WO | 02/10501 A1 | | 2/2002 |
| WO | 2004/042136 | * | 5/2004 |
| WO | 2004/069137 A2 | | 8/2004 |
| WO | 2006/067225 A1 | | 6/2006 |

OTHER PUBLICATIONS

Liang et al., "Solid Polymer Electrolytes. IV. Preparation and Characterization of Novel Crosslinked Epoxy-Siloxane Polymer Complexes as Polymer Electrolytes," Journal of Polymer Science: Part A: Polymer Chemistry, vol. 40, 2002, pp. 1226-1235.

* cited by examiner

*Primary Examiner* — Margaret Moore
(74) *Attorney, Agent, or Firm* — Rankin, Hill & Clark LLP

(57) ABSTRACT

The invention concerns polyamino and/or polyammonium/polysiloxane copolymer compounds with polyalkylene oxide units in comb-shaped arrangement, a method for producing said compounds and their use, in particular for treating textiles and other natural or synthetic textile materials.

16 Claims, No Drawings

POLYAMINO AND/OR POLYAMMONIUM/POLYSILOXANE COPOLYMER COMPOUNDS WITH POLYALKYLENE OXIDE UNITS IN COMB-SHAPED ARRANGEMENT

The invention relates to polyamino- and/or polyammonium-polysiloxane copolymer compounds with polyalkylene oxide units in a comblike arrangement, to processes for their preparation and to their use, especially for treatment of textiles and other natural and synthetic fibrous materials.

Polysiloxanes containing amino groups are known as textile softeners (EP 441 530).

It is also known that α,ω-epoxy-modified siloxanes can be reacted with α,ω-amino-functionalized alkylene oxides, and these products can be used as hydrophilic softeners (U.S. Pat. No. 5,807,956, U.S. Pat. No. 5,981,681). In a further development of this concept, block copolymers in which α,ω-epoxy-modified siloxanes and α,ω-epoxy-modified polyethers are bonded to one another via primary alkylamines as chain extenders have been proposed (U.S. Pat. No. 6,475,568). Advantages of these compounds are said to be relatively high softness and substrate wetting capacity.

Aminosiloxanes with ethylene oxide/propylene oxide units in the side chains have likewise been described (U.S. Pat. No. 5,591,880, U.S. Pat. No. 5,650,529).

An enhanced substantivity is expected from polysiloxane quats ("polysiloxane quats"=polysiloxanes containing quaternary ammonium groups). The reaction of α,ω-diepoxides with tertiary amines in the presence of acids affords α,ω-diquaternary siloxanes which can be used for haircare purposes (DE-A-37 19 086). In addition to tetraalkyl-substituted quaternary ammonium structures, aromatic imidazolinium derivatives are also claimed.

A reduction in the washout from hair can be achieved when the α,ω-diepoxides are reacted with di-tertiary amines in the presence of acids to give long-chain polyquaternary polysiloxanes (EP-A-282720). Aromatic quaternary ammonium structures are not disclosed.

Such polyquaternary imidazolinium derivatives are considered in U.S. Pat. No. 6,240,929. These cationic compounds are said to have a further enhanced compatibility with respect to the anionic surfactants present in cosmetic formulations. However, the washout resistance from hair is based on the brief attack by principally water and very mild surfactants which do not irritate the skin, while wash-resistant hydrophilic softeners for textiles have to withstand the attack of concentrated surfactant solutions with high grease and soil detachment capacity. An additional complicating factor is that modern washing compositions comprise strongly alkaline complexing agents, bleaches with oxidative action and complex enzyme systems, and the fibers are often exposed to the action at elevated temperatures over hours.

Introduction of alkylene oxide groups in addition to the quat structures is thought to enhance the hydrophilicity.

Strictly comblike alkylene oxide-modified polysiloxane quats have likewise been described. The hydroxyl groups of polyethersiloxanes substituted in a comblike manner are converted to the corresponding chlorine derivatives with epichlorohydrin (U.S. Pat. No. 5,098,979) or chloroacetic acid (U.S. Pat. No. 5,153,294, U.S. Pat. No. 5,166,297). This is followed by quaternization with tertiary amines. The disadvantage of the solutions according to U.S. Pat. No. 5,098,979, U.S. Pat. No. 5,153,294 and U.S. Pat. No. 5,166,297 is that the quat groups, as a result of the alkylene oxide units, are positioned far removed from the main chain, as a result of which the substantivity of the overall molecule is weakened.

Branched alkylene oxide-modified polysiloxane quats have been synthesized from α,ω-OH-terminated polysiloxanes and trialkoxysilanes by condensation. The quaternary ammonium structure is introduced via the silane, the quaternary nitrogen atom being substituted by alkylene oxide units (U.S. Pat. No. 5,602,224). The disadvantage of this solution is the relatively inflexible coupling of quat content and degree of branching.

U.S. Pat. No. 6,242,554 describes α,ω-difunctional siloxane derivatives which each have a separate quaternary ammonium and alkylene oxide unit. These monoquaternary compounds, however, not sufficiently substantive.

WO 02/10257 and WO 02/10259 claim polyquaternary polysiloxane block copolymers as progressive softeners which enable softening of textiles during finishing and also, alternatively, during the washing process from detergent formulations. US-A 2002/0103094 considers the use of the silicone materials mentioned in textile care formulations. WO 02/10257, WO 02/10259 and US-A 2002/0103094 disclose materials in which the quat groups are present partly or fully separated from the alkylene oxide units. These alkylene oxide units are incorporated into the block copolymer as α,ω-difunctional units.

WO 03/78504 describes branched polyquaternary polysiloxane block copolymers as permanent textile softeners. The branching units incorporated may include trifunctional alkylene oxide structures which are present separated from the quat groups. As a result of their crosslinker character, these trifunctional alkylene oxides can be introduced only to a restricted degree.

Proceeding from this prior art, a further improvement in the hydrophilicity of the silicone-based block copolymers without sacrificing the achievable softness of the treated fibers, especially with uniform or improved substantivity (adhesion of the siloxane systems on the fiber), in the flexibility in the formulation of the siloxane systems and in the administration form, especially in the direction of a reduction in the use amounts needed and the material costs is very desirable.

It is thus an object of the invention to provide polyquaternized siloxane block copolymers for treatment of textiles and other natural and synthetic fibrous materials, for example paper fibers, wool and hair, which impart a softness typical of silicones, an improved elasticity and reduced creasing tendency combined with enhanced hydrophilicity to such materials or substrates, preferably textile materials.

It is a further object of the invention to describe the use of the inventive substances as part of systems for textile initial finishing, as softeners in laundry detergent systems based on anionic and/or nonionic surfactants, in separate softener systems for fiber treatment after the performance of the fiber wash, as part of softener systems for nonwovens such as paper and textiles, as an ironing aid and composition for preventing or reversing textile creases, as part of formulations for treatment of hard surfaces, such as glass, ceramic, plastic, for example automobiles, and as part of cosmetic systems for treatment of hair and skin.

It has been found that, surprisingly, polyamino- and/or polyammonium-polysiloxane copolymer compounds, characterized in that they have repeat units of the formula (I):

$$-[Q-V]-\qquad (I)$$

in which Q is selected from the group which consists of:
—NR—,
—N$^+$R$_2$—
a saturated or unsaturated diamino-functional heterocycle of the formulae:

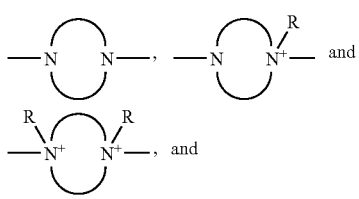

an aromatic diamino-functional heterocycle of the formula:

a trivalent radical of the formula:

a trivalent radical of the formula:

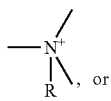

or a tetravalent radical of the formula

in which R is in each case hydrogen or a monovalent organic radical, where Q does not bind to the carbonyl carbon atom, V is selected from the group which consists of $V^1$, $V^2$ and $V^3$, in which $V^2$ is selected from divalent straight-chain, cyclic or branched, saturated, unsaturated or aromatic hydrocarbon radicals which have up to 1000 carbon atoms (not counting the carbon atoms of the polysiloxane radical $Z^2$ defined below) and may optionally contain one or more groups selected from

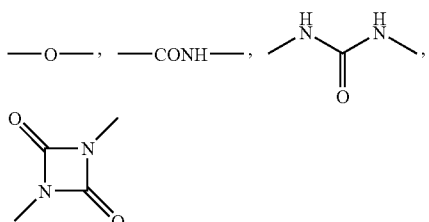

—CONR$^2$—, in which R$^2$ is hydrogen, a monovalent straight-chain, cyclic or branched, saturated, unsaturated or aromatic hydrocarbon radical which has up to 100 carbon atoms, may contain one or more groups selected from —O—, —NH—, —C(O)— and —C(S)— and may optionally be substituted by one or more substituents selected from the group which consists of a hydroxyl group, an optionally substituted heterocyclic group preferably containing one or more nitrogen atoms, amino, alkylamino, dialkylamino, ammonium, polyether radicals and polyether ester radicals, where, when a plurality of —CONR$^2$ groups are present, they may be the same or different, —C(O)— and —C(S), the $V^2$ radical may optionally be substituted by one or more hydroxyl groups and/or by

in which a is an integer from 0 to 2 and R and R' may be the same or different from one another and are each an organic radical, and the $V^2$ radical contains at least one —$Z^2$— group of the formula

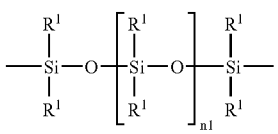

in which $R^1$ may be the same or different and is selected from the group which consists of: $C_1$- to $C_{22}$-alkyl, fluoro($C_1$-$C_{10}$)alkyl, $C_6$-$C_{10}$-aryl and —W—Si(OR)$_{3-a}$(R')$_a$ in which R, R' and a are each as defined above and W is —O— or a divalent straight-chain, cyclic or branched, saturated, unsaturated or aromatic hydrocarbon which has up to 100 carbon atoms and may contain one or more —C(O)—, —O—, —NH—, —S— groups, and may optionally be substituted by hydroxyl groups, and $n_1$=from 20 to 1000, $V^1$ is selected from divalent straight-chain, cyclic or branched, saturated, unsaturated or aromatic hydrocarbon radicals which have up to 1000 carbon atoms and may optionally contain one or more groups selected from

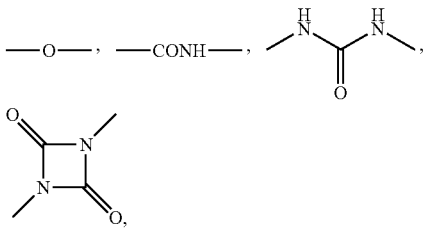

—CONR$^2$—, in which R$^2$ is as defined above, where the R$^2$ groups in the $V^1$ and $V^2$ groups may be the same or different, —C(O)—, —C(S)— and —$Z^1$— in which —$Z^1$— is a group of the formula

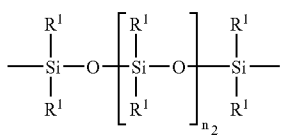

in which
R¹ is as defined above, where the R¹ groups in the V¹ and V² groups may be the same or different, and
n₂=from 0 to 19,
and the V¹ radical may optionally be substituted by one or more hydroxyl groups and/or by

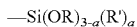

in which a is an integer of 0 to 2 and R and R' may be the same or different from one another and are each an organic radical, and
V³ is a trivalent or higher-valency, straight-chain, cyclic or branched, saturated, unsaturated or aromatic hydrocarbon radical which has up to 1000 carbon atoms and optionally contains one or more groups selected from

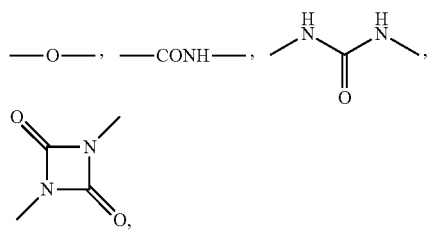

—CONR² in which R² is as defined above, —C(O)—, —C(S)—, —Z¹— which is as defined above, —Z²— which is as defined above, and Z³ in which Z³ is a trivalent or higher-valency organopolysiloxane unit, and
which may optionally be substituted by one or more hydroxyl groups and/or by

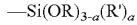

in which a is an integer from 0 to 2 and R and R' may be the same or different from one another and are each an organic radical,
with the proviso
that the polysiloxane compound mentioned contains at least one —Z¹—, —Z²— or —Z³— group,
that the trivalent and tetravalent Q radicals either serve to branch the main chain formed from Q and V such that the valencies which do not serve for binding in the main chain bear further branches formed from -[Q-V]— units, or the trivalent and tetravalent Q radicals are saturated by V³ radicals within a linear main chain without formation of a branch, and
that at least one R radical in the Q groups is a polyalkylene oxide-containing organic radical R°,
and in which the positive charges which result from ammonium groups are neutralized by organic or inorganic acid anions,
can solve the objective described above.

In a preferred embodiment, the inventive polyamino- and/or polyammonium-polysiloxane copolymer compounds are characterized in that the molar R°:Q ratio is from 0.001 to 2, more preferably from 0.01 to 1, more preferably from 0.05 to 0.8. When the molar ratio is less than 0.001, the hydrophilicity is too low. An optimal balance of softness and hydrophilicity is possible in the range from 0.05 to 0.8.

The R° radical is preferably a group of the formula (III):

in which X is a single bond or a divalent straight-chain, branched or cyclic hydrocarbon radical which has up to 20 carbon atoms and may optionally contain nitrogen and/or oxygen, and X is bonded to the nitrogen atom of Q via a carbon atom,
E is a polyalkylene oxide radical of the formula

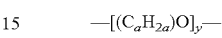

in which a=from 2 to 4,
y=from 2 to 10 000,
which is bonded to the X group via a carbon atom and to the Y group via an oxygen atom,
Y is hydrogen or a monovalent straight-chain, branched or cyclic, saturated, unsaturated or aromatic hydrocarbon radical which has up to 24 carbon atoms and may contain oxygen and/or nitrogen and/or halogen and is bonded to the E group via a carbon atom.

R° is preferably a group of the formula (III) in which -E- is a group of the formula (IV):

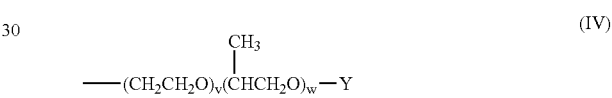

which may comprise random and blockwise sequences of the ethylene oxide and propylene oxide units and the bond to E may be via an ethylene oxide or propylene oxide unit, the illustration of group (IV) hence being only quantitative,
where
v=from 0 to 200,
w from 0 to 200,
v+w≧1.
In the group of the formula (III), moreover, Y is preferably selected from H and straight-chain, cyclic, branched C₁- to C₂₂-alkyl, alkenyl, alkynyl, fluoro(C₁-C₁₀)alkyl and C₆-C₁₀-aryl radicals.

Further preferred alkylene oxide units R° preferably have the structure:

where
v=from 0 to 200,
w=from 0 to 200,
v+w≧1,
Y=H or straight-chain, cyclic, branched C₁- to C₂₂-alkyl, alkenyl, alkynyl, fluoro(C₁-C₁₀)alkyl and C₆-C₁₀-aryl radicals.

Preferably, in the above general polyalkylene oxide formulae:
v is from 0 to 100, more preferably from 0 to 70, especially from 0 to 40, very especially from 0 to 20,
w is from 0 to 100, more preferably from 0 to 70, especially from 0 to 40, very especially from 0 to 20, Y is a straight-chain, cyclic, branched $C_1$- to $C_{12}$-alkyl radical, alkenyl radical, alkynyl radical or $C_6$-$C_{10}$-aryl radical, especially methyl, ethyl, isopropyl, butyl, hexyl, dodecyl, allyl, oleyl, phenyl.

A further preferred alkylene oxide unit $R^o$ has the structure

—($C_1$-$C_{12}$)-alkylene-$N^+R_2EY$ in which $C_1$-$C_{12}$-alkylene is a straight-chain, cyclic or branched alkylene unit having from 1 to 12 carbon atoms, and R, E and Y are each as defined above.

The polysiloxane compounds which, on average, contain at least two, preferably at least three, even more preferably at least four, units of the formula (I), preference being given to the presence of an average of at least two, more preferably at least three, even more preferably at least four, $R^o$ units, and an average of at least one $V^1$, $V^2$ and/or $V^3$ unit, are preferably terminated by monofunctional -Q-R and/or —V—R groups, i.e., for example, by amino groups. These arise through saturation of one of the two bonding sites of Q and V by a monovalent R group or hydrogen as defined above, and are referred to hereinafter as $V^{st}$ or $Q^{st}$. Other unconverted reactive groups such as epoxy or haloalkyl groups may also be present in place of $V^{st}$.

In the inventive polysiloxane compounds which contain an average of at least two units of the formula (I), an average of at least $R^o$ units and an average of at least one $V^1$, $V^2$ and/or $V^3$ unit being present, are, for example, linear polysiloxane copolymers of the general formula (I'):

-[Q-V]—           (I')

in which Q is as defined above,
V and at least one $V^1$ group or V group is,
in which $V^1$ and $V^2$ are each as defined above. In addition, V may also be trivalent or higher-valency, particularly trivalent, $V^3$ radicals. In this case, preference is also given to the presence of trivalent or tetravalent Q units as defined above, and the saturation of the trivalent or higher-valency $V^3$ radicals and of the trivalent or tetravalent Q units is preferably effected exclusively among one another within the linear main chain to form cyclic structures as explained below in more detail. However, this case is less preferred.

In the general formulae (I) or (I') the molar ratio of the $V^1$ and $V^2$ groups in the polysiloxane compounds $V^2/V^1$ may in principle assume any value. The invention thus also includes the case in which the polysiloxane compound of the formulae (I) or (I') contains only $V^2$ units, i.e. the polysiloxane compound has the formula -[Q-$V^2$]—. The case in which the polysiloxane compound contains only $V^1$ units is also included in the invention. In this case, the $V^1$ units must, however, contain $Z^1$-siloxane units.

In a preferred embodiment of the invention, the polysiloxane compound of the formulae (I) or (I'), however, contains both $V^2$ and $V^1$ units.

In a further preferred embodiment of the present invention, the molar ratio of the $V^1$ and $V^2$ groups in the polysiloxane compounds of the general formulae (I) and (I') is:

$V^2/V^1 = 1$.

In a further embodiment of the linear polysiloxane compounds of the formula (I) or (I'), $V^2/V^1$ does not equal 1; $V^2/V^1$ is preferably <1, more preferably <0.9; even more preferably, $V^2/V^1$ satisfies the relationship $0.0005 < V^2/V^1 < 0.5$, even more preferably $0.0005 < V^2/V^1 < 0.3$.

The R group is preferably selected from the $R^2$ groups.
Preferred embodiments of Q are:
For radicals of the formula

a quaternized imidazole unit of the structure

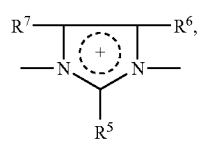

a quaternized pyrazole unit of the structure

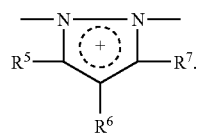

For radicals of the formula

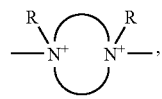

a diquaternized piperazine unit of the structure

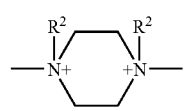

For radicals of the formula

a monoquaternized piperazine unit of the structure

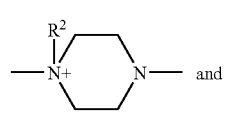

a monoquaternized piperazine unit of the structure

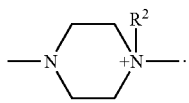

For radicals of the formula

—N⁺R₂—, a diquaternized unit of the structure

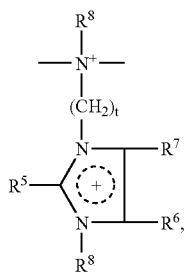

a monoquaternized unit of the structure

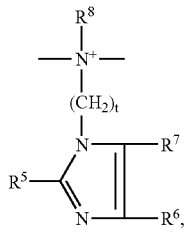

a diquaternized unit of the structure

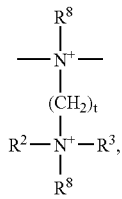

and a monoquaternized unit of the structure

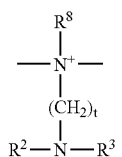

For radicals of the formula

—NR—, a monoquaternized unit of the structure

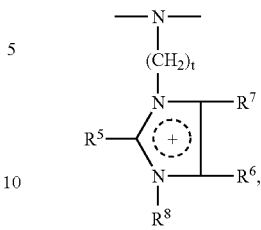

a monoquaternized unit of the structure

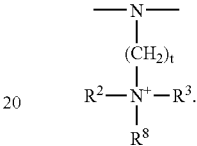

In which:
t is from 2 to 10,
R is as defined above, preferably $R^2$, $R^2$ is as defined above, and the definition of $R^2$ may be the same as or different from the definition of the above $R^2$ group,
$R^3$ is as defined for $R^2$, where $R^2$ and $R^3$ may be the same or different, or
$R^2$ and $R^3$, together with the positively charged nitrogen atom, form a five- to seven-membered heterocycle which may optionally additionally have one or more nitrogen, oxygen and/or sulfur atoms,
$R^5, R^6, R^7$ may the same or different and are selected from the group which consists of: H, halogen, hydroxyl group, nitro group, cyano group, thiol group, carboxyl group, alkyl group, monohydroxyalkyl group, polyhydroxyalkyl group, thioalkyl group, cyanoalkyl group, alkoxy group, acyl group, acetyloxy group, cycloalkyl group, aryl group, alkylaryl group, and groups of the —NHR$^w$ type in which R$^w$ is H, alkyl group, monohydroxyalkyl group, polyhydroxyalkyl group, acetyl group, ureido group, and in each case two of the adjacent $R^5$, $R^6$ and $R^7$ radicals with the carbon atoms bonding them to the heterocycle may form aromatic five- to seven-membered rings, and
$R^8$ is as defined for $R^2$, where $R^8$ and $R^2$ may be the same or different. In particular, $R^8$ may be a polyoxyalkylene-containing radical, which leads to the formation of an $R^o$-containing Q radical.

In the case that Q is a trivalent radical of the formulae

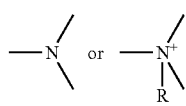

or a tetravalent radical

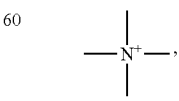

these radicals in the linear copolymers of the formula (I'), as mentioned above, preferably do not serve to branch the polysiloxane copolymers, but rather these radicals are bonded exclusively to especially trivalent $V^3$ radicals to form cyclic structures which are part of the linear main chain, for example a structural element of the formula:

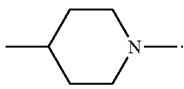

In a preferred embodiment of the polysiloxane compounds of the formula (I) or (I'), V is a group of the formula

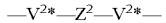

in which $Z^2$ is as defined above and $V^{2*}$ is a divalent straight-chain, cyclic or branched, saturated, unsaturated or aromatic hydrocarbon radical which has up to 40 carbon atoms and may optionally contain one or more groups selected from —O—, —CONH—, —CONR$^2$— in which $R^2$ is as defined above, —C(O)— and —C(S)—, and the $V^{2*}$ radical may optionally be substituted by one or more hydroxyl groups.

In the aforementioned embodiment, the inventive linear polysiloxane copolymer may have the following repeat units:

—[$V^{2*}$—$Z^2$—$V^{2*}$-Q]-, preferably together with
—[$V^1$-Q]-.

The molar ratio of the repeat units —[$V^{2*}$—$Z^2$—$V^{2*}$-Q]- to —[$V^1$-Q]-, i.e. the $V^2/V^1$ ratio, may, as mentioned above, be about 1, but in one embodiment is preferably unequal to 1, more preferably >1, even more preferably >1 and less than 1.5. The introduction of the hydrophilic $R^o$ side groups in the form of a comb enables the proportion of the $V^2$ group which contributes to softening properties to be increased with equal hydrophilicity. Conversely, for a given proportion of softening $V^2$ groups, it is possible to increase the hydrophilicity by introducing the $R^o$ group.

As will be explained in detail below in connection with the process for preparing the above-described linear polysiloxane copolymers, the blockwise sequences which have more than one —[$V^1$-Q]- unit bonded to one another, according to the preparation method, may be bonded regularly to the $V^2$-Q units or irregularly to the $V^2$-Q units.

This means the following:
In the regular compound in which, for example, a prepolymer corresponding to the -Q-[$V^1$-Q]$_x$- group is reacted with monomer units corresponding to $V^2$ in a molar ratio of 1:1, the linear polysiloxane copolymers can be represented as follows:

—{$V^2$-Q-[$V^1$-Q]$_x$-}$_y$-.

In this formula, x may be from 2 to 2000 and is the mean of the distribution, and y is likewise a mean and is from 2 to 1000.

In general, the inventive polysiloxane polymers therefore preferably have the formula -[Q-V]$_{y'}$— in which y' is from 2 to 1000, more preferably from 3 to 500, even more preferably from 4 to 200.

The linear polysiloxane copolymers represented by the formula —{$V^2$-Q-[$V^1$-Q]$_x$-}$_y$- are characterized in that they have essentially no —$V^2$-Q- units bonded to one another or, in other words, two —$V^2$-Q- units are always interrupted by at least one —$V^1$-Q- unit.

In the irregular compound in which, for example, monomers corresponding to Q units are reacted with monomer units corresponding to $V^1$ and monomer units corresponding to $V^2$ in a ratio of $Q/(V^1+V^2)$, where, for example, $V^2/V^1>1$, the linear polysiloxane copolymers can be represented as follows:

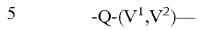

in which, in V, the $V^2/V^1$ ratio is then >1. In this case, the $V^1$ and $V^2$ groups are distributed randomly over the copolymer chain. In contrast to the linear polysiloxane copolymers prepared by the regular compound, this copolymer may also have adjacent -Q-$V^2$— units.

In a preferred embodiment of the polysiloxane compound of the formula (I) or (I') used in accordance with the invention, the $V^1$ group is selected from divalent straight-chain, cyclic or branched, saturated, unsaturated or aromatic hydrocarbon radicals which have up to 600, preferably up to 400, carbon atoms and may optionally contain one or more groups selected from

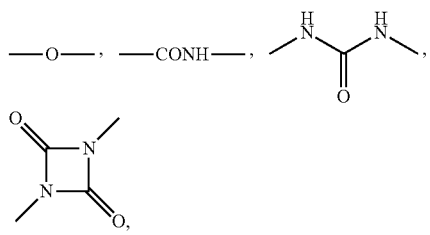

—CONR$^2$, in which $R^2$ is as defined above, —C(O)—, —C(S)— and —$Z^1$—, in which —$Z^1$— is a group of the formula

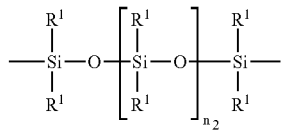

in which
$R^1$ is $C_1$-$C_{18}$-alkyl which may optionally be substituted by one or more fluorine atoms, or phenyl, and $n_2$ is as defined above.

In a further preferred embodiment of the polysiloxane compounds of the formula (I) or (I'), the Q group is selected from:

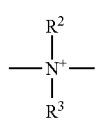

in which $R^2$ is preferably H or alkyl, preferably having from 1 to 6 carbon atoms, and $R^3$ is preferably H, alkyl, preferably having from 1 to 6 carbon atoms, or $R^o$.

Preferably, in the formulae (I) and (I'):
$R^1$=$C_1$- to $C_{18}$-alkyl, especially methyl, ethyl, trifluoropropyl and phenyl,
$n_1$=from 20 to 400, more preferably from 20 to 300, especially from 20 to 200. In a further preferred embodiment, $n_1$ is between 20 and 50 or between 80 and 200. The number $n_1$ is the mean degree of polymerization from $M_n$ of the diorganosiloxy units in the $Z^2$ group.

$n_2$=from 0 to 15, more preferably from 0 to 10, especially from 0 to 5, more especially 0. The number $n_2$ is the mean degree of polymerization from $M_n$ of the diorganosiloxy units in the $Z^1$ group.

More preferably,

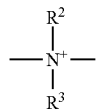

is —$NH_2^+$—, —$N(CH_3)_2^+$—, —$(NHR^\circ)^+$—.

$V^{2*}$ is a divalent straight-chain, cyclic or branched, saturated, unsaturated or aromatic hydrocarbon radical which has up to 16 carbon atoms and may contain one or more groups selected from —O—, —CONH—, —$CONR^2$— in which $R^2$ is as defined above: —C(O)—, —C(S)—, and may be substituted by one or more hydroxyl groups. Even more preferably, —$V^{2*}$— is selected from groups of the formulae:

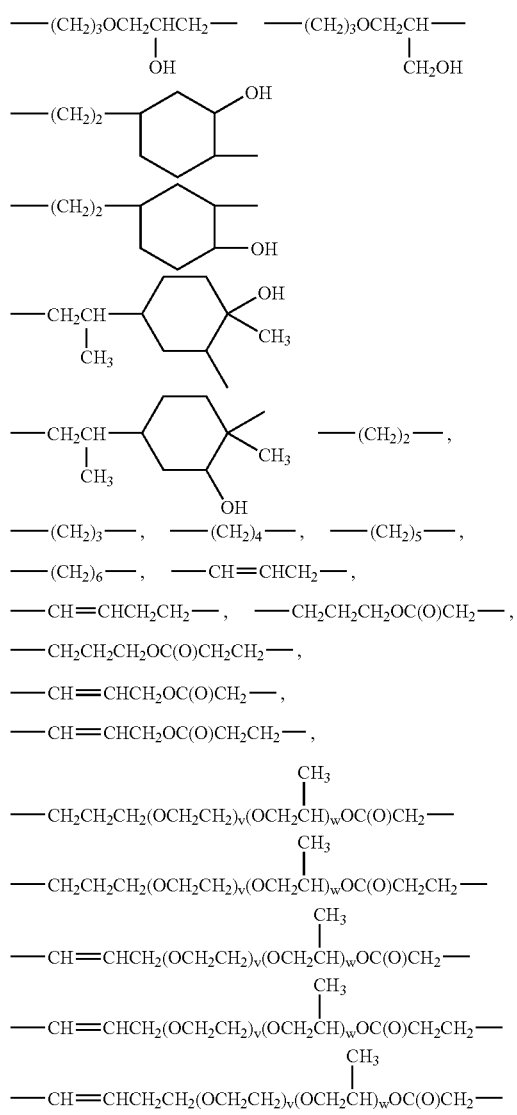

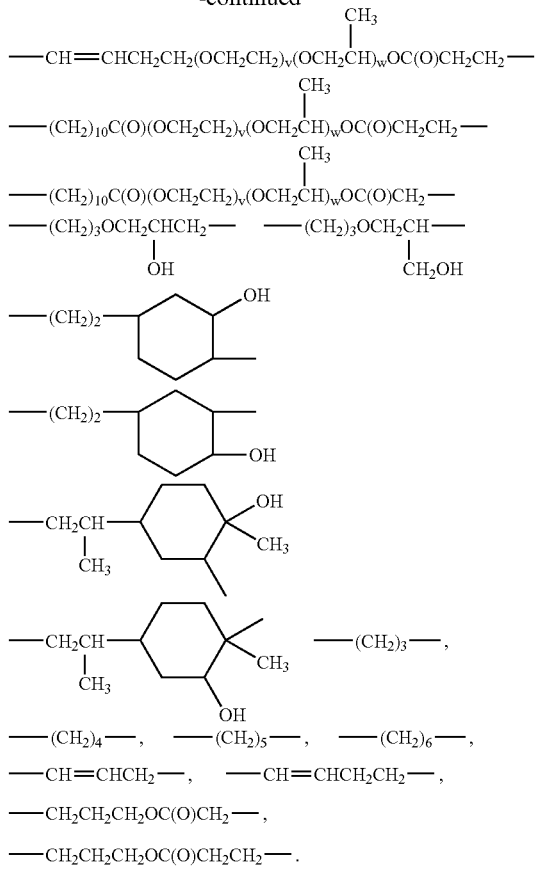

with $v + w \geq 0$, $V^1$ is preferably
—$R^9$—
in which $R^9$ is a divalent saturated or mono- or polyunsaturated, straight-chain or branched hydrocarbon radical having from two to 25 carbon atoms,
—$(CH_2)_u$C(O)O—[$(CH_2CH_2O)_q$—$(CH_2CH(CH_3)O)_r$]—C(O)$(CH_2)_u$—
—$(CH_2)_u$C(O)O—$R^9$—O—C(O)$(CH_2)_u$— in which $R^9$ is as defined above,
—$(CH_2)_u$—$R^{10}$—$(CH_2)_u$— in which $R^{10}$ is an aromatic group,
—$[CH_2CH_2O]_q$—$[CH_2CH(CH_3)O]_r$—$CH_2CH_2$—,
—$CH(CH_3)CH_2O[CH_2CH_2O]_q$—$[CH_2CH(CH_3)O]_r$—$CH_2CH(CH_3)$—
—$CH_2CH(OH)CH_2$—,
—$CH_2CH(OH)(CH_2)_2CH(OH)CH_2$—,
—$CH_2CH(OH)CH_2OCH_2CH(OH)CH_2OCH_2CH(OH)CH_2$— and
—$CH_2CH(OH)CH_2O$—$[CH_2CH_2O]_q$—$[CH_2CH(CH_3)O]_r$—$CH_2CH(OH)CH_2$—
in which
u is from 1 to 3,
q and r are from 0 to 200, preferably from 0 to 100, more preferably from 0 to 70 and especially preferably from 0 to 40, and
q+r>0.

Preferred variants of $V^1$ are structures of the formula:
—$CH_2C(O)O$—$[CH_2CH_2O]_q$—$[CH_2CH(CH_3)O]_r$—C(O)$CH_2$—, —CH$_2$CH$_2$C(O)O—[CH$_2$CH$_2$O]$_q$—[CH$_2$CH(CH$_3$)O]$_r$—C(O)CH$_2$CH$_2$—,
—CH$_2$CH$_2$CH$_2$C(O)O—[CH$_2$CH$_2$O]$_q$—[CH$_2$CH(CH$_3$)O]$_r$—C(O)CH$_2$CH$_2$CH$_2$—,
esterified alkylene, alkenylene, alkynylene units, especially of the structures
—CH$_2$C(O)O—[CH$_2$]$_o$—OC(O)CH$_2$—,
—CH$_2$CH$_2$C(O)O—[CH$_2$]$_o$—OC(O)CH$_2$CH$_2$—,
—CH$_2$CH$_2$CH$_2$C(O)O—[CH$_2$]$_o$—OC(O)CH$_2$CH$_2$CH$_2$—
—CH$_2$C(O)O—CH$_2$C≡CCH$_2$—OC(O)CH$_2$—,
—CH$_2$CH$_2$C(O)O—CH$_2$C≡CCH$_2$—OC(O)CH$_2$CH$_2$—,
—CH$_2$CH$_2$CH$_2$C$_2$C(O)O—CH$_2$C≡CCH$_2$—OC(O)CH$_2$CH$_2$CH$_2$—,
—CH$_2$C(O)O—CH$_2$CH═CHCH$_2$—OC(O)CH$_2$—,
—CH$_2$CH$_2$C(O)O—CH$_2$CH═CHCH$_2$—OC(O)CH$_2$CH$_2$—,
—CH$_2$CH$_2$CH$_2$C(O)O—CH$_2$CH═CHCH$_2$—OC(O)CH$_2$CH$_2$CH$_2$—,
alkylene, alkenylene, alkynylene and aryl units, especially of the structures:

—[CH$_2$]$_o$— where o=from 2 to 6,
—CH$_2$C≡CCH$_2$—, —CH$_2$CH═CHCH$_2$—, —CH(CH$_3$)CH$_2$CH$_2$—,

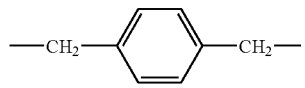

polyalkylene oxide units, especially of the structures
—[CH$_2$CH$_2$O]$_q$—[CH$_2$CH(CH$_3$)O]$_r$CH$_2$CH$_2$—,
—CH(CH$_3$)CH$_2$O[CH$_2$CH$_2$O]$_q$—[CH$_2$CH(CH$_3$)O]$_r$—CH$_2$CH(CH$_3$)—
with
mono-, di- or polyhydroxy-functional units, especially of the structures
—CH$_2$CH(OH)CH$_2$—, —CH$_2$CH(OH)(CH$_2$)$_2$CH(OH)CH$_2$—,
—CH$_2$CH(OH)CH$_2$OCH$_2$CH(OH)CH$_2$OCH$_2$CH(OH)CH$_2$—,
—CH$_2$CH(OH)CH$_2$O—[CH$_2$CH$_2$O]$_q$—[CH$_2$CH(CH$_3$)O]$_r$—CH$_2$CH(OH)CH$_2$—
where
q=from 0 to 200,
r=from 0 to 200.
Preferably, q=from 1 to 50, in particular from 2 to 50, especially from 1 to 20, very especially from 1 to 10, and 1 or 2, r=from 0 to 100, in particular from 0 to 50, especially from 0 to 20, very especially from 0 to 10, and 0 or 1 or 2.

The inventive polysiloxanes may be prepared, for example, by a process in which
a) a primary amine which contains a polyalkylene oxide group and optionally further amine compounds are reacted with amino-reactive polysiloxane-containing compounds and optionally further amino-reactive compounds, or
b) the amino group of a polyamino-polysiloxane copolymer (starting) compound is alkylated with an alkylating agent which contains a polyalkylene oxide group.

Suitable selection of the stoichiometry of the starting compounds allows the ratio of the $V^1$, $V^2$, $R^o$ groups in the inventive compounds to be controlled.

Suitable monomers which introduce $V^1$ are, for example, alpha,omega-diamines with internal $V^1$ units, such as alkylenediamines or diaminopolyethers. These are reacted, for example, with amino-reactive monomers containing $V^2$ and/or $R^o$ groups, for example diepoxy polysiloxane compounds, dihaloalkyl polysiloxane compounds, monoamino polyethers. Alternatively, $V^1$ can also be introduced via dihaloalkyl compounds, diepoxide compounds or compounds with mixed groups which are reacted with amino-functional monomers which introduce the $V^2$, $R^o$ groups or further $V^1$ groups.

For the preparation, reference may be made, for example, to WO 02/10257.

The inventive polysiloxanes of the general formula (I) may contain branching units $V^3$. $V^3$ is a trivalent or higher-valency straight-chain, cyclic or branched, saturated, unsaturated or aromatic hydrocarbon radical which has up to 1000 carbon atoms and may optionally contain one or more groups selected from —O—, —CONH—, —CONR$^2$— in which R$^2$ is as defined above, —C(O)—, —C(S)—, —Z$^1$— which is as defined above, —Z$^2$— which is as defined above, and Z$^3$, in which Z$^3$ is a trivalent or higher-valency organopolysiloxane unit. The branching unit $V^3$ may be silicone-free. Examples thereof include:

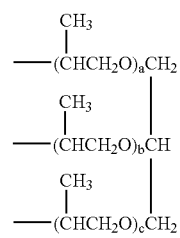

in which a, b and c may be the same or different and may be from 1 to 40,

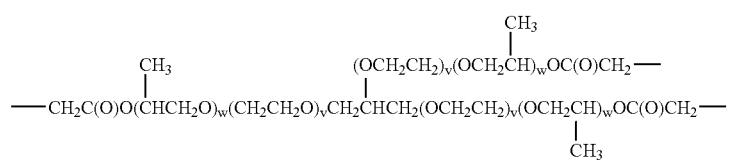

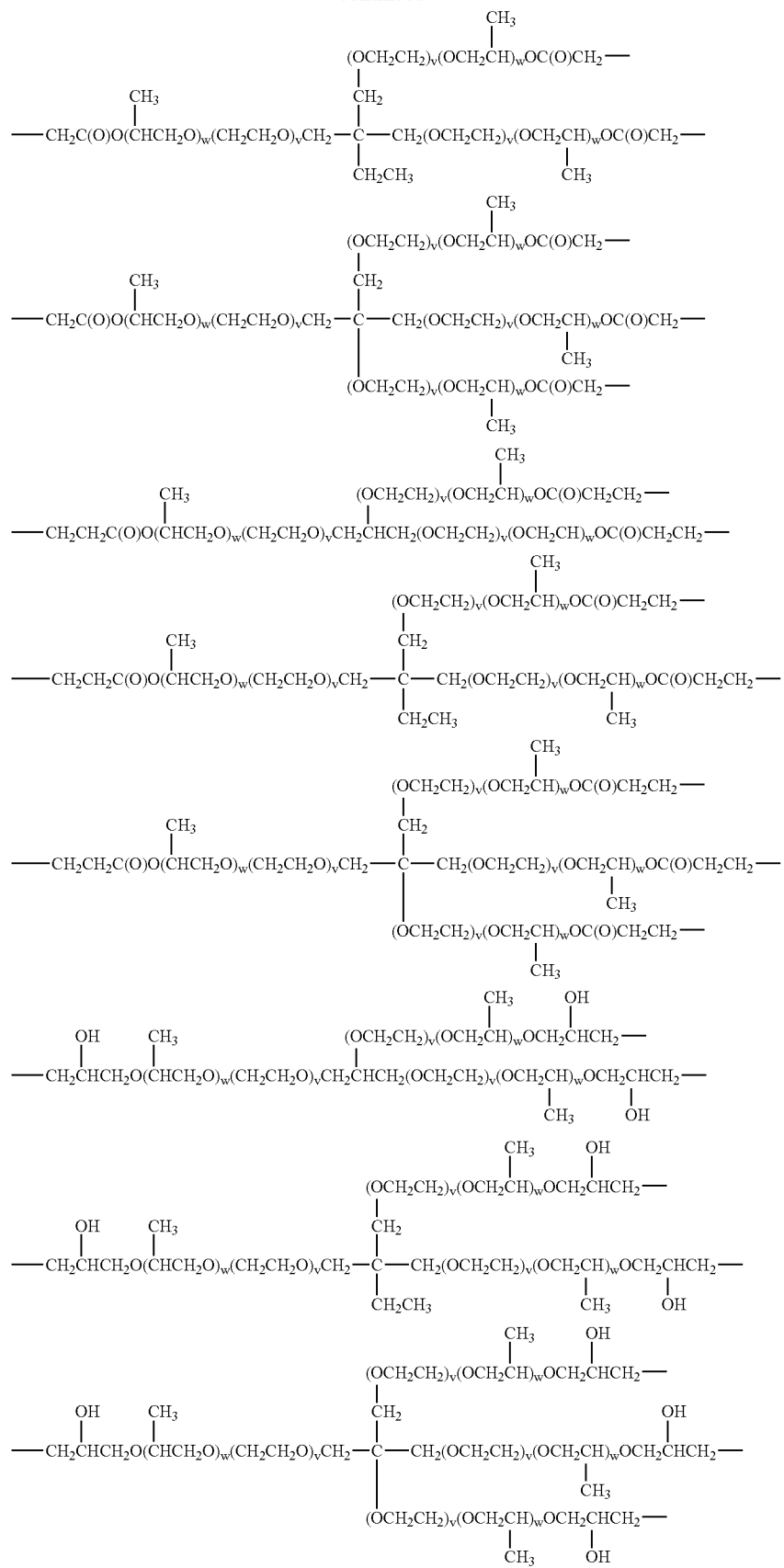

where v+w≧0, where the arrangement of the ethylene oxide and propylene oxide units may be random or blockwise, and the attachment to Q may be via ethylene oxide and propylene oxide units via a carbon atom.

The branching unit $V^3$ may contain a trivalent or higher-valency organopolysiloxane unit, for example:

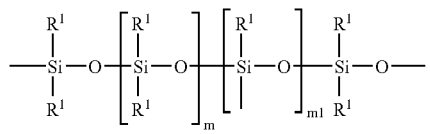

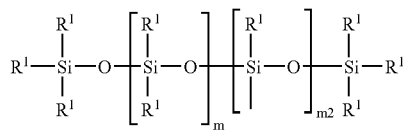

in which $R^1$ is as defined above, m=from 0 to 1000, and $m^1 \geq 1$ and $m^2 \geq 3$,

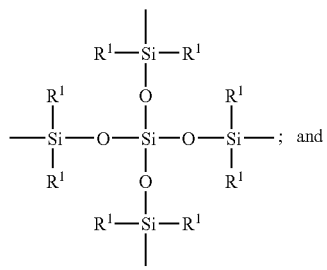

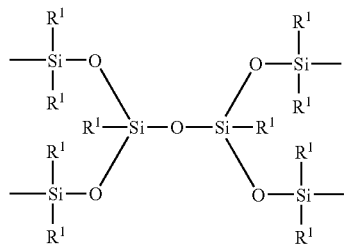

in which $R^1$ is in each case as defined above.

One example of a $Z^3$-containing branching unit $V^3$ is, for example:

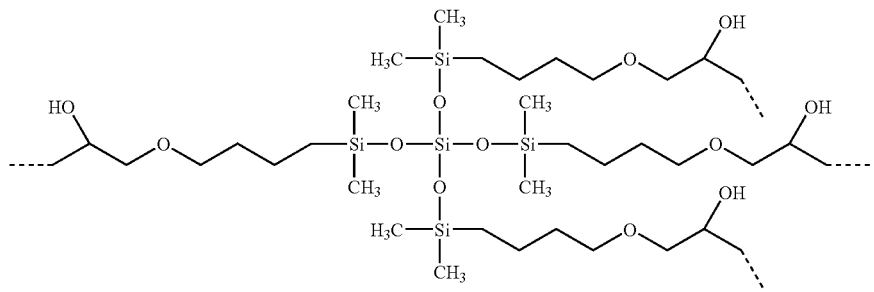

The inventive polysiloxanes contain the $R^o$ units, which are preferably bonded into the polymer by suitable alkylating reactions of primary, secondary or tertiary monoamino-functionalized polyalkylene oxides with reactively functionalized siloxane precursors. Preference is given to using the monoprimary functionalized Jeffamine® of the M series (Huntsman Corp.).

In a preferred embodiment, the primary monoamino-functionalized polyalkylene oxides are alkylated in a preceding reaction initially with the reactively functionalized siloxanes, preferably epoxysiloxanes, to tertiary amines. These precursors are bonded into the siloxane block copolymer in the subsequent polymer formation reaction. In another preferred variant, it is possible to dispense with this preceding reaction and to use the primary monoamino-functionalized polyalkylene oxides directly in the polymer formation reaction.

For the less preferred case that the polyalkylene oxide units should terminate the siloxane block polymers in a controlled manner, the starting materials may be secondary or tertiary amino-functionalized polyalkylene oxide units. When they are not available directly, they can be prepared by prereaction of the primary mono-amino-functionalized polyalkylene oxides with alkylating agents, for example monoepoxides such as isopropyl glycidyl ether or dimethyl sulfate.

The monofunctionally attached hydrophilic element $R^o$ is introduced into the inventive polyquaternary polysiloxane copolymers in order to enhance the hydrophilicity in a controlled manner. This leads both to enhanced hydrophilicity of the inventive polysiloxane copolymers themselves, such that, for example, more stable emulsions in water form, and to an increase in the hydrophilicity of the substrates treated with the inventive polysiloxane copolymers, which, for example, leads to an improved moisture absorption.

It is within the scope of the present invention to apply the introduction of monofunctionally attached hydrophilic units to alternating polysiloxane quat block copolymers known per se (DE-A 3340708, U.S. Pat. No. 6,240,929, EP 282720, DE-A 10036533).

It is within the scope of the invention to combine the introduction of monofunctionally attached hydrophilic units with the known introduction of difunctional hydrophilic units into the main polymer chain (WO 02/10257; WO 02/10259).

It is also within the scope of the invention to combine the introduction of monofunctionally attached hydrophilic units with the likewise known introduction of trifunctional and higher-functionality units into the main polymer chain (WO 03/078504).

It is also within the scope of the invention to combine the introduction of monofunctionally attached hydrophilic units with the likewise known introduction of highly charged oligomerized quat structures into the main polymer chain (WO 2004/041912, WO 2004/042136).

It is also within the scope of the invention to combine the introduction of monofunctionally attached hydrophilic units with the likewise described introduction of reactive units into the main polymer chain (application PCT/EP 2004/050472). Such reactive groups include groups of the following formulae:

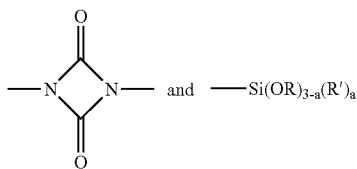

in which 'a' is an integer from 0 to 2 and R and R' may be the same or different and are each an organic radical. The reactive groups mentioned may, in accordance with the invention, be introduced via units corresponding to V or Q, as described in detail in PCT/EP 2004/050472. In a preferred embodiment, the —Si(OR)$_{3-a}$(R')$_a$ group may, for example, be introduced via the use of primary or secondary amines of the formula NR$_2$—(C1-C12)alkylene-Si(OR)$_{3-a}$(R')$_a$ in which R is as defined above, as likewise explained in detail in PCT/EP 2004/050472. The reactive —Si(OR)$_{3-a}$(R')$_a$ group is then disposed on the repeat units Q.

It is likewise within the scope of the invention to combine the introduction of monofunctionally attached hydrophilic units with a plurality of the abovementioned concepts.

The inventive quaternary ammonium compounds may be solid or liquid at 25° C. In the case that they are liquid at 25° C., the viscosities of the polysiloxanes mentioned are preferably between 500 to 50 000 000 mPa·s at 25° C., preferably from 1000 to 2 500 000 mPa·s at 25° C., and at a shear rate of D=1 s$^{-1}$.

The invention further relates to the use of the inventive compounds for fiber treatment or fiber finishing.

The invention further relates to the use of the inventive compounds for initial finishing and treatment of textiles and other natural and synthetic fibrous materials, including paper, hair and wool.

The inventive compounds are likewise suitable for treatment of textiles and other natural and synthetic fibrous materials in compositions for fiber pretreatment and especially in washing composition formulations comprising nonionic and/or anionic surfactants. For this purpose, the inventive compounds may be incorporated directly into washing compositions or else be metered separately into the running washing process. As a result of the use of the inventive compounds during the wash process, a silicone-typical softness, an improved elasticity and reduced creasing tendency are imparted to the treated substrates while retaining acceptable hydrophilicity.

Moreover, the inventive compounds may find use as part of separate softener systems after the washing of fibers and textiles, as an ironing aid and composition for preventing and reversing textile creases.

The invention further relates to the use of the inventive compounds for treatment and finishing of hard surfaces such as glass, ceramic, tiles, plastics surfaces, metal surfaces, paint surfaces, especially automobile bodies, very especially in dryer formulations for machine automobile washing.

It is also possible to introduce the inventive formulations into cosmetic systems for treatment of hair and skin.

The invention further relates to aqueous emulsions which comprise at least one inventive polyamino- and/or polyammonium-polysiloxane copolymer compounds, and also optionally one or more surfactants and optionally one or more nitrogen-free polysiloxane compounds, and to the use of the aqueous emulsions mentioned in one of the abovementioned applications.

EXAMPLES

Example 1

(Introduction of Monofunctionally Attached Hydrophilic Units in Combination with the Introduction of Difunctional Hydrophilic Units)

A 500 ml three-neck flask is initially charged with 173.7 g (30 mmol) of a siloxane epoxide of the structure

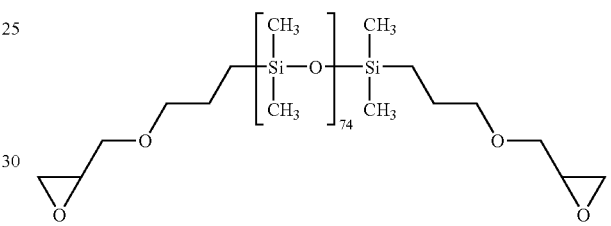

4.17 g (4 mmol) of the monofunctional aminopolyether Jeffamine® M 1000 of the structure H$_2$N[CH(CH$_3$)CH$_2$O]$_3$(CH$_2$CH$_2$O)$_{19}$CH$_3$
and 30 ml of 2-propanol, and heated to 80° C. with stirring for 6 hours.

To this mixture is added a mixture consisting of
8.51 g (4 mmol) of the difunctional aminopolyether Jeffamine® ED 2003 of the structure H$_2$NCH(CH$_3$)CH$_2$[OCH$_2$CH(CH$_3$)]$_a$(OCH$_2$CH$_2$)$_{38.7}$[OCH$_2$CH(CH$_3$)]$_b$NH$_2$
where a+b=6,
3.79 g (22 mmol) of N,N,N',N'-tetramethyl-1,6-hexanediamine
1.68 g (28 mmol) of acetic acid
5.6 g (28 mmol) of dodecanoic acid
6 ml of 2-propanol
24 ml of deionized water.

This overall mixture is heated to 80° C. for 8 h, becomes clear in the course of the reaction and turns orange-brown. 250 g of a polymer with the following structural elements are obtained:

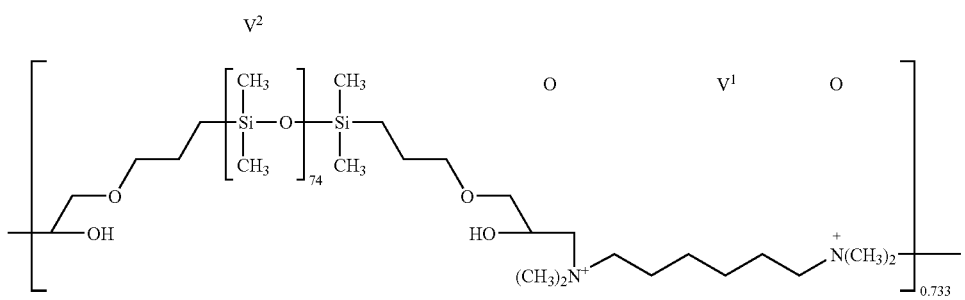

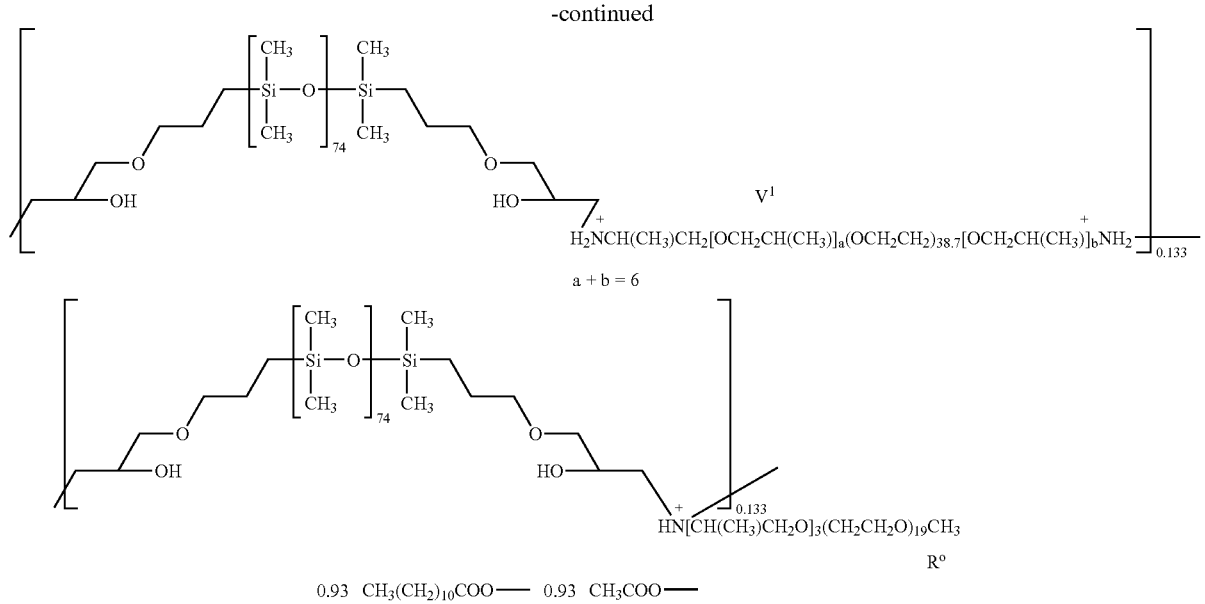

0.93 CH$_3$(CH$_2$)$_{10}$COO— 0.93 CH$_3$COO—

(V1, V2, Q and R° exhibit, by way of example, the repeat units or radicals of the formula (I)).

Example 2

(Introduction of Monofunctionally Attached Hydrophilic Units in Combination with Polymer Endstopping)
A 500 ml three-neck flask is initially charged with 156.33 g (27 mmol) of a siloxane epoxide of the structure

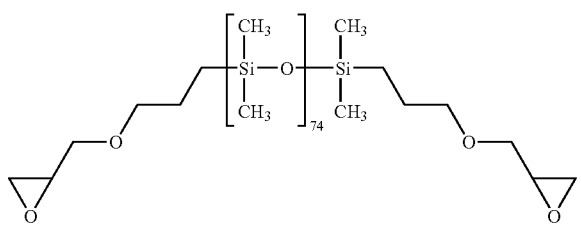

6.25 g (6 mmol) of the monofunctional aminopolyether Jeffamine® M 1000 of the structure H$_2$N[CH(CH$_3$)CH$_2$O]$_3$(CH$_2$CH$_2$O)$_{19}$CH$_3$ and 30 ml of 2-propanol, and heated to 80° C. with stirring for 6 hours.

0.7 g (6 mmol) of isopropyl glycidyl ether is added to the mixture.

Subsequently added to this mixture is a mixture consisting of 4.14 g (24 mmol) of N,N,N',N'-tetramethyl-1,6-hexanediamine 1.62 g (27 mmol) of acetic acid 5.4 g (27 mmol) of dodecanoic acid 6 ml of 2-propanol 24 ml of deionized water.

This overall mixture is heated to 80° C. for 8 hours. 214 g of a light-brown to orange solution are obtained. The polymer contains the following structural elements:

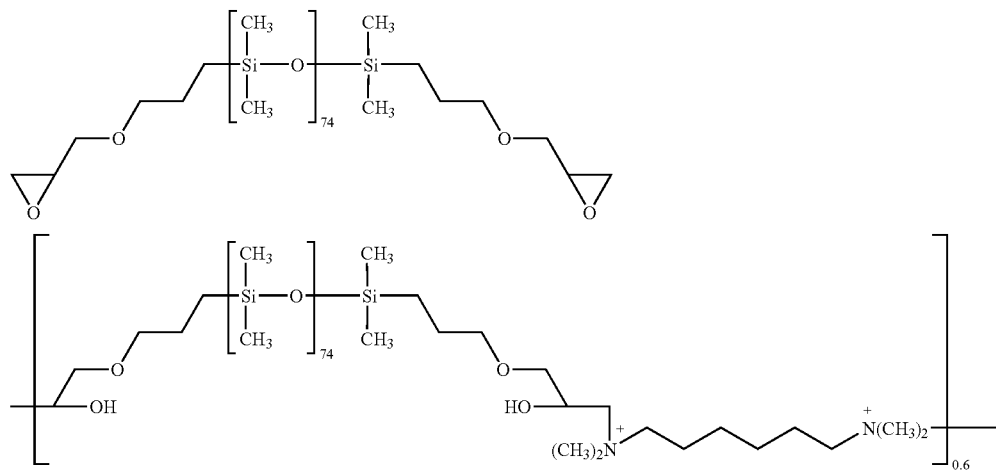

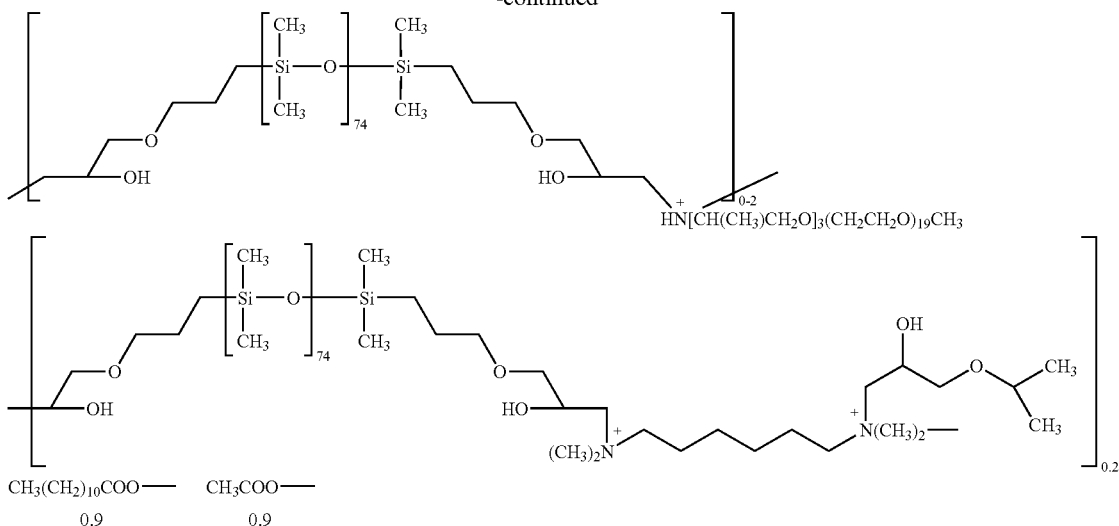

Example 3

(Introduction of Monofunctionally Attached Hydrophilic Units in Combination with the Introduction of Difunctional Hydrophilic Units and Branching Hydrophilic Units)

A 500 ml three-neck flask is initially charged with 173.7 g (30 mmol) of a siloxane epoxide of the structure

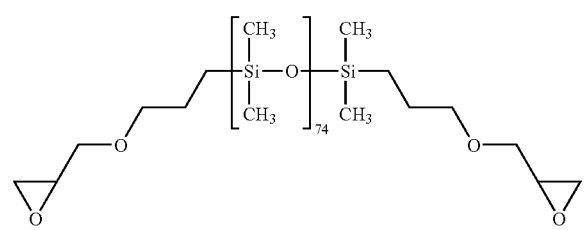

4.17 g (4 mmol) of the monofunctional aminopolyether Jeffamine® M 1000 of the structure $H_2N[CH(CH_3)CH_2O]_3$ $(CH_2CH_2O)_{19}CH_3$ and 30 ml of 2-propanol, and heated to 80° C. with stirring for 6 hours.

To this mixture is added a mixture consisting of 6.38 g (3 mmol) of the difunctional aminopolyether Jeffamine® ED 2003 of the structure $H_2NCH(CH_3)CH_2[OCH_2CH$ $(CH_3)]_a(OCH_2CH_2)_{38.7}[OCH_2CH(CH_3)]_bNH_2$ where a+b=6

2.1 g (0.66 mmol) of the trifunctional aminopolyether Jeffamine® T3000 of the structure

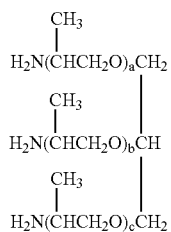

where a+b+c=50

3.79 g (22 mmol) of N,N,N',N'-tetramethyl-1,6-hexanediamine 1.68 g (28 mmol) of acetic acid 5.6 g (28 mmol) of dodecanoic acid 6 ml of 2-propanol 24 ml of deionized water.

This overall mixture is heated to 80° C. for 8 hours. 237.3 g of an orange-brown solution are obtained. The polymer contains the following structural elements:

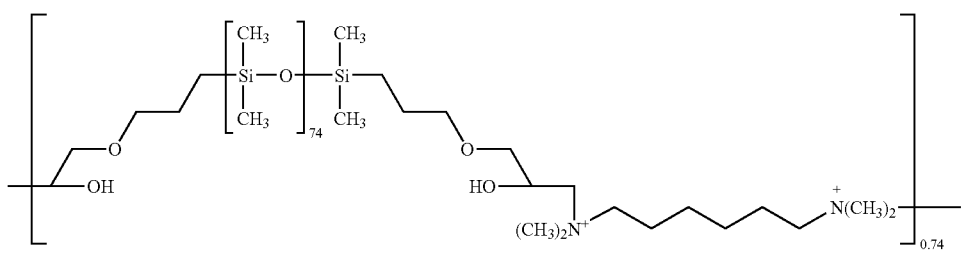

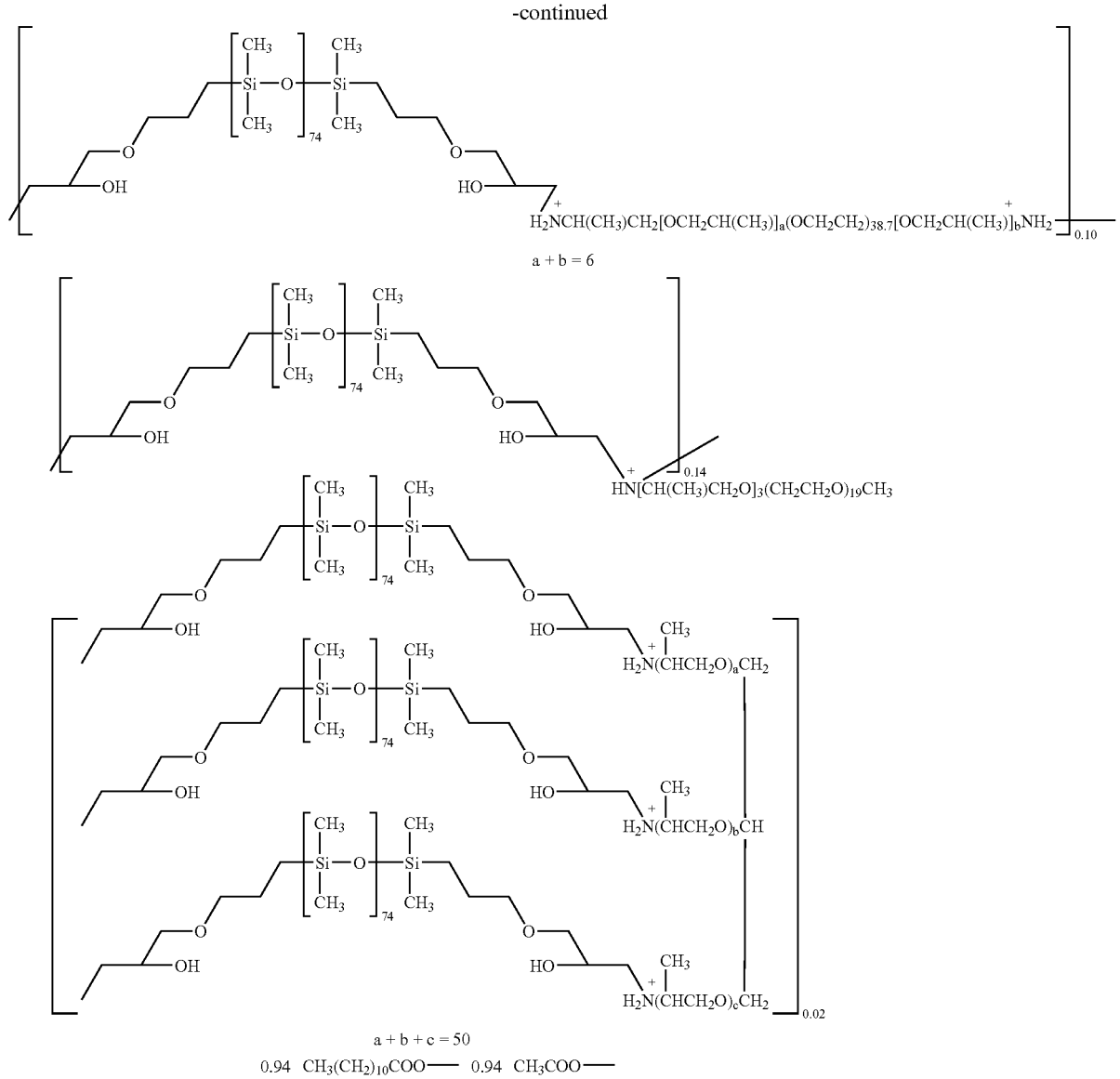

Example 4

Introduction of Monofunctionally Attached Hydrophilic Units in Combination with the Introduction of Difunctional Hydrophilic Units and Reactive Units)

4a) Preparation of a Uretdione-Containing Ditertiary Amine

In a 100 ml three-neck flask, 4.36 g (9.8 mmol) of isophorone diisocyanate dimer of the structure

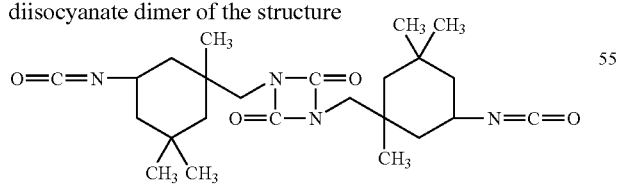

are dissolved at from 30 to 40° C. in 10.17 g of methoxypropyl acetate. With stirring, 2 g (19.6 mmol) of N,N-dimethyl-1,3-propanediamine are added dropwise within 20 minutes, in the course of which the temperature rises to from 70 to 80° C. Cooling results in phase separation. Addition of 1.24 g of 2-propanol affords a solution which is clear at room temperature. The amino-modified isophorone diisocyanate dimer has the structure

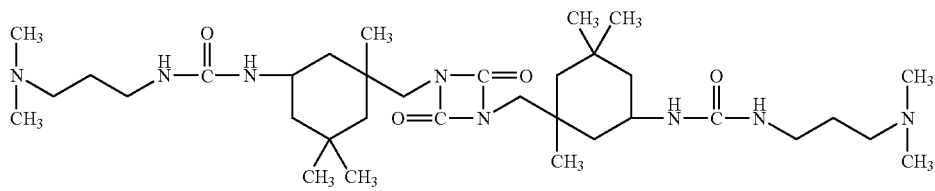

Example 4b

A 500 ml three-neck flask is initially charged with 173.7 g (30 mmol) of a siloxane epoxide of the structure

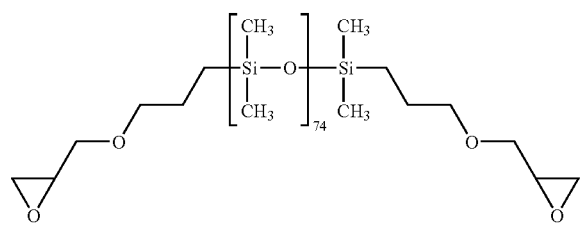

4.17 g (4 mmol) of the monofunctional aminopolyether Jeffamine® M 1000 of the structure $H_2N[CH(CH_3)CH_2O]_3(CH_2CH_2O)_{19}CH_3$ and 30 ml of 2-propanol, and heated to 82-84° C. with stirring for 5 hours.

To this mixture is added a mixture consisting of
8.51 g (4 mmol) of the difunctional aminopolyether Jeffamine® ED 2003 of the structure
$H_2NCH(CH_3)CH_2[OCH_2CH(CH_3)]_a(OCH_2CH_2)_{38.7}$
$[OCH_2CH(CH_3)]_bNH_2$
where a+b=6
3.41 g (19.8 mmol) of N,N,N',N'-tetramethyl-1,6-hexanediamine
1.68 g (28 mmol) of acetic acid
5.6 g (28 mmol) of dodecanoic acid
6 ml of 2-propanol
24 ml of deionized water.

Subsequently, 4 g (2.2 mmol) of the uretdione-containing ditertiary amine according to Example 4a are added to the mixture and the overall mixture is heated to 82-84° C. for 8 hours. 250 g of product are obtained. The polymer contains the following structural elements:

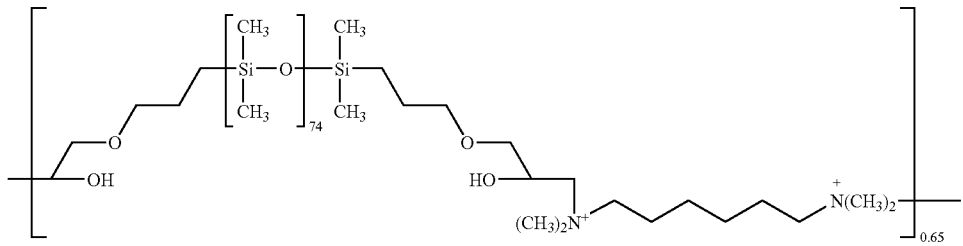

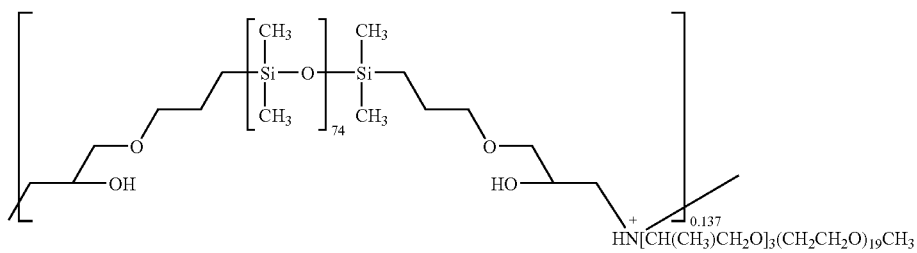

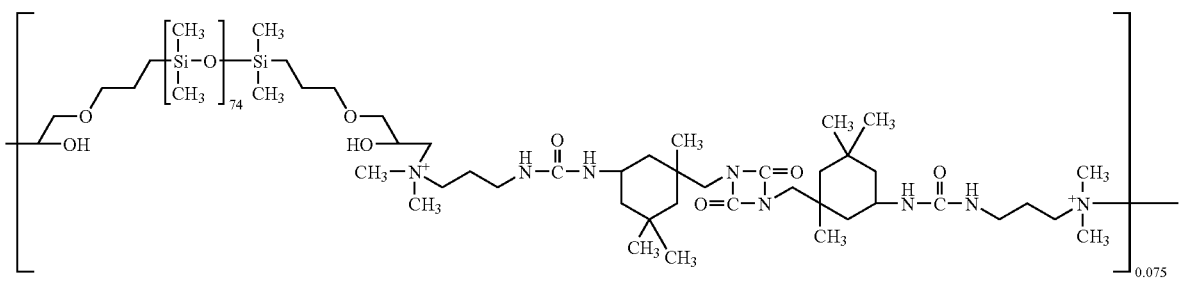

-continued

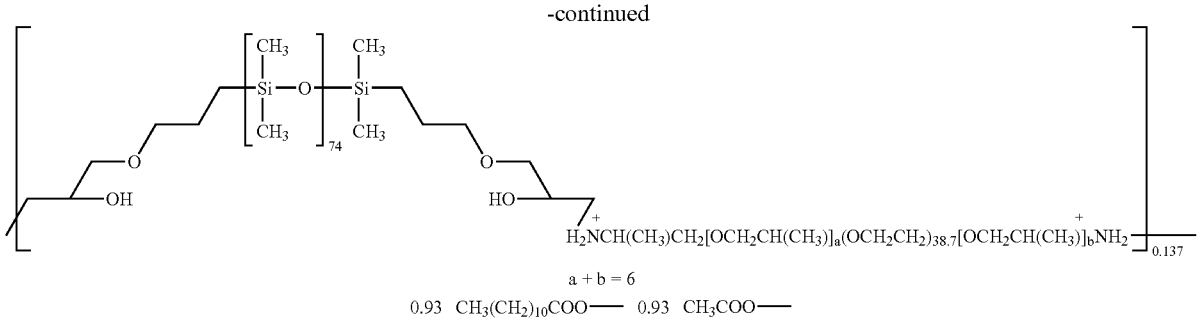

a + b = 6
0.93 CH$_3$(CH$_2$)$_{10}$COO—— 0.93 CH$_3$COO——

Example 5

(Introduction of Monofunctionally Attached Hydrophilic Units with a Quaternary Ammonium Group Integrated into the Chain)

Example 5a

Preparation of a Chloroacetic Ester 205.3 g (0.5 mol) of a molar mass-distributed octaethylene glycol monoallyl ether are initially charged at room temperature 20° C. under nitrogen. With vigorous stirring, 63.4 g (0.55 mol) of chloroacetyl chloride are added dropwise within 20 minutes. During the dropwise addition, the temperature rises to 67° C. and intensive HCl evolution sets in. After the dropwise addition has ended, the mixture is heated to 120° C. for 1 hour. Finally, all constituents which boil up to 120° C. at 20 hPa were distilled off. 246 g of a pale yellow ester of the structure
ClCH$_2$C(O)O(CH$_2$CH$_2$O)$_8$CH$_2$CH═CH$_2$ were obtained.

Example 5b

A 500 ml three-neck flask is initially charged with 173.7 g (30 mmol) of a siloxane epoxide of the structure

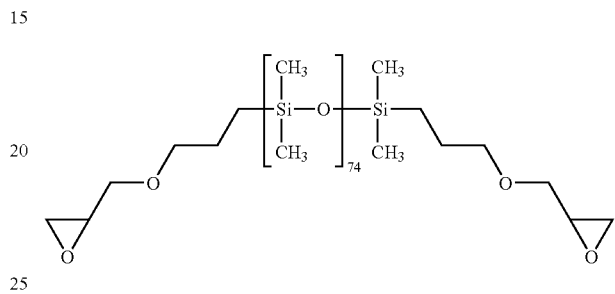

0.92 g (9 mmol) of N,N-dimethylpropylenediamine and 100 ml of 2-propanol, and heated to 82-84° C. with stirring for 5 hours.

Subsequently, 4.38 g (9 mmol) of the chloroacetic ester according to Example 5a) are added dropwise and the mixture is heated to 82-84° C. for a further 5 hours.

To this mixture is added a mixture consisting of
3.62 g (21 mmol) of N,N,N',N'-tetramethyl-1,6-hexanediamine
1.26 g (21 mmol) of acetic acid
4.2 g (21 mmol) of dodecanoic acid
6 ml of 2-propanol
24 ml of deionized water.

The overall mixture is heated to 82-84° C. for 8 hours. 361 g of a biphasic product are obtained. The polymer contains the following structural features:

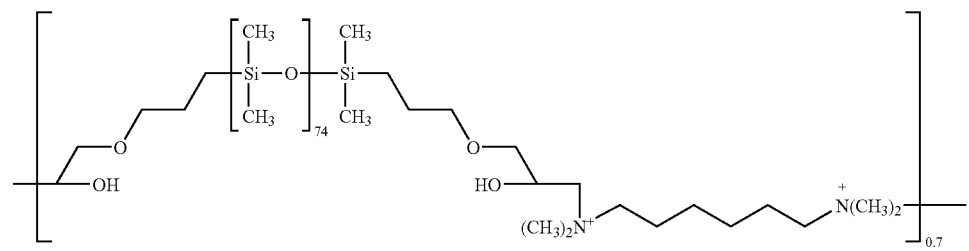

-continued

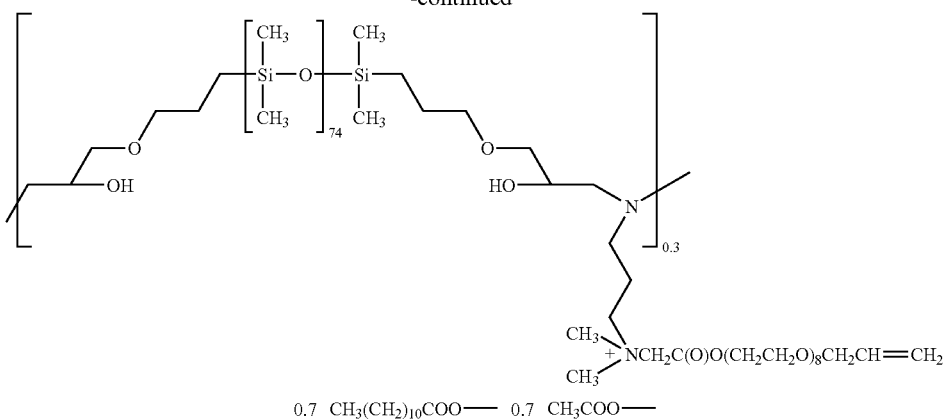

0.7 CH₃(CH₂)₁₀COO— 0.7 CH₃COO—

Example 6

(Introduction of Monofunctionally Attached Hydrophilic Units)

A 500 ml three-neck flask is initially charged with 184.5 g (15 mmol) of a siloxane epoxide of the structure

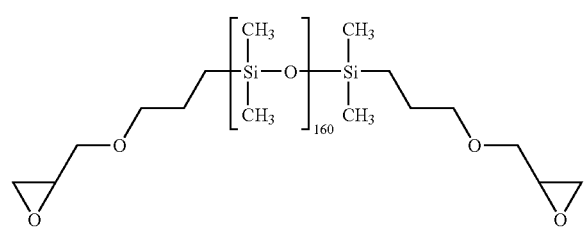

6.25 g (3 mmol) of the monofunctional aminopolyether Jeffamine® M 2070 of the structure H₂N[CH(CH₃)CH₂O]₁₀(CH₂CH₂O)₃₂CH₃ and 20 g of dipropylene glycol monobutyl ether, and heated to from 100 to 103° C. for 6 hours.

To this mixture is added a mixture consisting of 2.07 g (12 mmol) of N,N,N',N'-tetramethyl-1,6-hexanediamine 0.9 g (15 mmol) of acetic acid 3.0 g (15 mmol) of dodecanoic acid 5.5 g of dipropylene glycol monobutyl ether 9.25 ml of deionized water.

This overall mixture is heated to 100-103° C. for 10 hours. 210 g of an 87.3% solution of a polymer with the following structural elements are obtained:

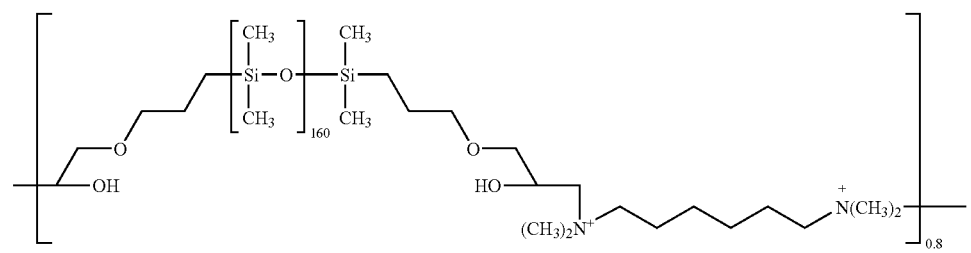

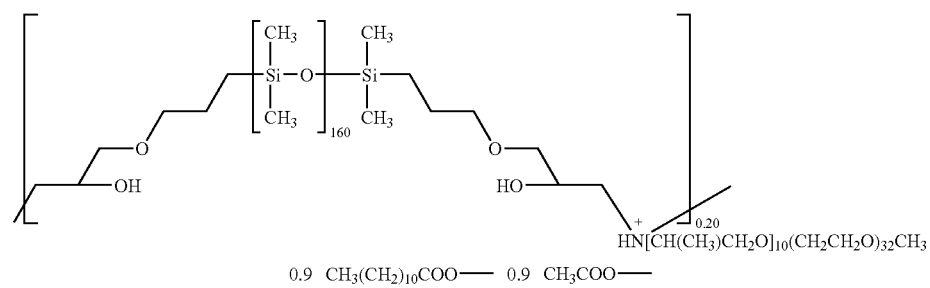

0.9 CH₃(CH₂)₁₀COO— 0.9 CH₃COO—

Example 7

Not Inventive (Introduction of Difunctionally Incorporated Hydrophilic Units)

A 500 ml three-neck flask is initially charged with 184.5 g (15 mmol) of a siloxane epoxide of the structure

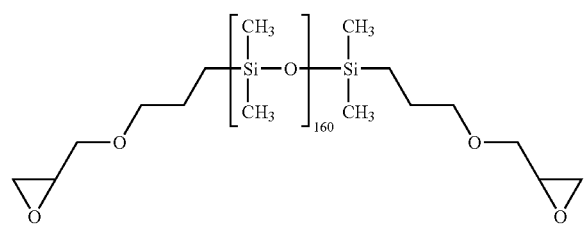

To this mixture is added a mixture consisting of
6.38 g (3 mmol) of the difunctional aminopolyether Jeffamine® ED 2003 of the structure
$H_2NCH(CH_3)CH_2[OCH_2CH(CH_3)]_a(OCH_2CH_2)_{38.7}[OCH_2CH(CH3)]_bNH_2$
where a+b=6
2.07 g (12 mmol) of N,N,N',N'-tetramethyl-1,6-hexanediamine
0.9 g (15 mmol) of acetic acid
3.0 g (15 mmol) of dodecanoic acid
25.5 g of dipropylene glycol monobutyl ether
9.25 ml of deionized water.

This overall mixture is heated to 100-103° C. for 10 hours. 205 g of an 86% solution of a polymer with the following structural elements is obtained:

Example 8

(Microemulsions)

The following 20% microemulsions are prepared:

TABLE 1

| | | Microemulsion 1 (inventive) | Microemulsion 2 (not inventive) |
|---|---|---|---|
| Siloxane quat solution (87.3% strength) according to Example 6 | [g] | 22.9 | — |
| Siloxane quat solution (86% strength) according to Example 7 | [g] | — | 23.3 |
| Renex ® 36 | [g] | 9.5 | 9.5 |
| Renex ® 30 | [g] | 2.05 | 2.05 |
| Crodet ® S40 | [g] | 1.0 | 1.0 |
| Acetic acid | [g] | 0.46 | 0.46 |
| Sodium acetate | [g] | 0.34 | 0.34 |
| Deionized water | [g] | 63.7 | 63.3 |

Renex ® 36: trade name of ICI Surfactants; tridecyl alcohol-$EO_{12}$-OH
Renex ® 30: trade name of ICI Surfactants; tridecyl alcohol-$EO_6$-OH
Crodet ® S40: trade name of Croda GmbH; stearic acid-$EO_{40}$-OH

Example 9

(Textile Finishing)

Bleached cotton terry fabric is finished in a Polymat (Mathis) for defined conditioning of the textiles with microemulsions 1 and 2 according to Example 8 under the following boundary conditions:

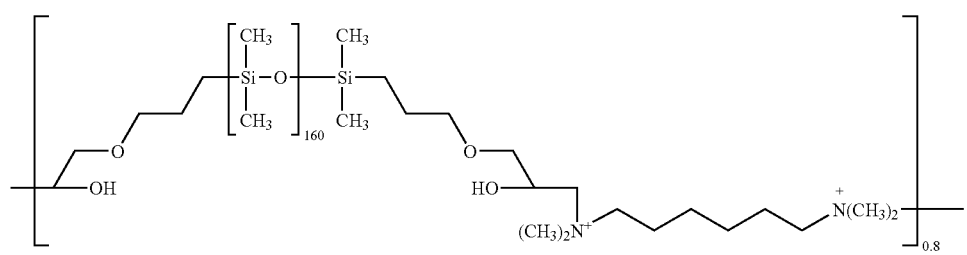

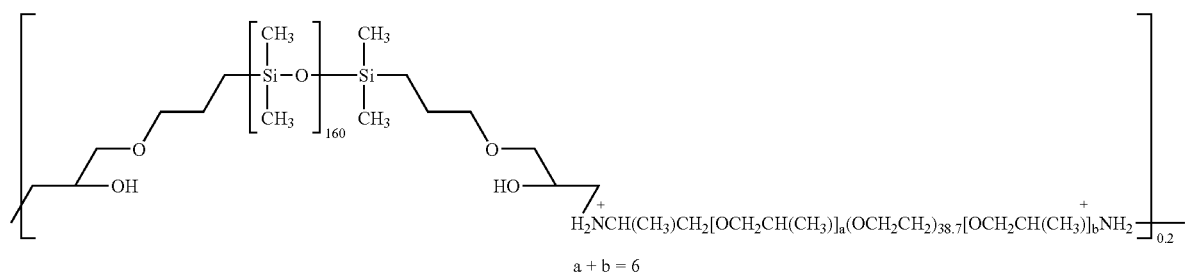

TABLE 2

| | |
|---|---|
| Concentration (mg of silicone quat/g of terry fabric) | 15 |
| Weight of cotton (g) | 10 |
| Amount of liquor (ml) | 300 |
| Finishing temperature (° C.) | 40 |
| Finishing time (min) | 30 |
| Mechanics (number of steel balls) | 21 |
| Drying temperature (° C.) | 80 |

To adjust the moisture content, the two specimens of cotton terry fabric are stored under atmospheric conditions for 24 hours.

Softness

Four test subjects compared the hand of the terry fabric specimens finished with microemulsions 1 and 2. No significant difference could be detected by any of the test subjects.

Hydrophilicity

50 μl water droplets are placed onto the terry fabric surface and the time until they sink in is measured in seconds.

TABLE 3

| | Dr1 | Dr2 | Dr3 | Dr4 | Dr5 | DrØ |
|---|---|---|---|---|---|---|
| Microemulsion 1 (inventive) | 1 | 1 | 2 | 1 | 1 | 1.2 |
| Microemulsion 2 (not inventive) | 3 | 2 | 3 | 3 | 4 | 3.0 |

The results show that, for materials with comparable alkylene oxide content, the hydrophilicity can be enhanced significantly by controlled use of monofunctionally attached alkylene oxide units without a noticeable adverse influence being exerted on the hand characteristics.

The invention claimed is:

1. A polyamino- and/or polyammonium-polysiloxane copolymer compound, characterized in that it has repeat units of the formula (I):

-[Q-V]—  (I)

in which Q is selected from the group which consists of:
   —NR—,
   —N$^+$R$_2$—
   a saturated or unsaturated diamino-functional heterocycle of the formulae:

an aromatic diamino-functional heterocycle of the formula:

a trivalent radical of the formula:

a trivalent radical of the formula:

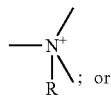

or a tetravalent radical of the formula

in which R is in each case hydrogen or a monovalent organic radical,
   where Q does not bind to the carbonyl carbon atom,
   V is selected from the group which consists of V$^1$, V$^2$ and V$^3$, in which
   V$^2$ is selected from divalent straight-chain, cyclic or branched, saturated, unsaturated or aromatic hydrocarbon radicals which have up to 1000 carbon atoms (not counting the carbon atoms of the polysiloxane radical Z$^2$ defined below) and may optionally contain one or more groups selected from

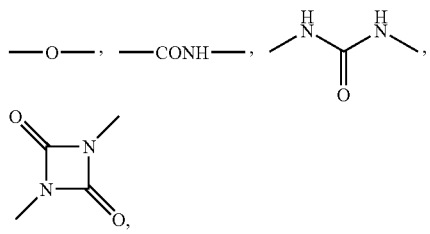

—CONR$^2$— in which R$^2$ is hydrogen, a monovalent straight-chain, cyclic or branched, saturated, unsaturated or aromatic hydrocarbon radical which has up to 100 carbon atoms, may contain one or more groups selected from —O—, —NH—, —C(O)— and —C(S)— and may optionally be substituted by one or more substituents selected from the group which consists of a hydroxyl group, an optionally substituted heterocyclic group preferably containing one or more nitrogen atoms, amino, alkylamino, dialkylamino, ammonium, polyether radicals and polyether ester radicals, where, when a plurality of —CONR$^2$ groups are present, they may be the same or different, —C(O)— and —C(S),
   the V$^2$ radical may optionally be substituted by one or more hydroxyl groups and/or by

in which a is an integer from 0 to 2 and R and R' may be the same or different from one another and are each an organic radical, and the $V^2$ radical contains at least one —$Z^2$— group of the formula

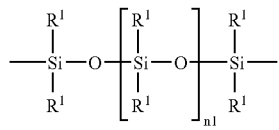

in which
R$^1$ may be the same or different and is selected from the group which consists of: $C_1$- to $C_{22}$-alkyl, fluoro($C_1$-$C_{10}$)alkyl, $C_6$-$C_{10}$-aryl and —W—Si(OR)$_{3-a}$(R')$_a$ in which R, R' and a are each as defined above and W is —O— or a divalent straight-chain, cyclic or branched, saturated, unsaturated or aromatic hydrocarbon which has up to 100 carbon atoms and may contain one or more —C(O)—, —O—, —NH—, —S— groups, and may optionally be substituted by hydroxyl groups, and
$n_1$=from 20 to 1000,
$V^1$ is selected from divalent straight-chain, cyclic or branched, saturated, unsaturated or aromatic hydrocarbon radicals which have up to 1000 carbon atoms and may optionally contain one or more groups selected from

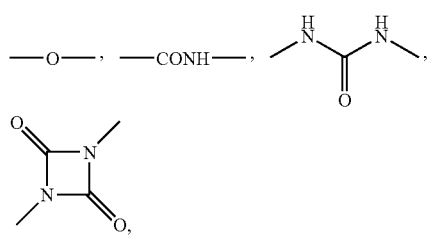

—CONR$^2$—, in which R$^2$ is as defined above, where the R$^2$ groups in the V$^1$ and V$^2$ groups may be the same or different,
—C(O)—, —C(S)— and —Z$^1$— in which —Z$^1$— is a group of the formula

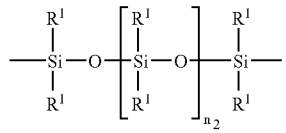

in which
R$^1$ is as defined above, where the R$^1$ groups in the V$^1$ and V$^2$ groups may be the same or different, and
$n_2$=from 0 to 19,
and the V$^1$ radical may optionally be substituted by one or more hydroxyl groups and/or by Si(OR)$_{3-a}$(R')$_a$ in which a is an integer of 0 to 2 and R and R' may be the same or different from one another and are each an organic radical, and
V$^3$ is a trivalent or higher-valency, straight-chain, cyclic or branched, saturated, unsaturated or aromatic hydrocarbon radical which has up to 1000 carbon atoms and optionally contains one or more groups selected from

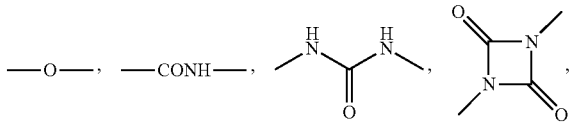

—CONR$^2$, in which R$^2$ is as defined above, —C(O)—, —C(S)—, —Z$^1$— which is as defined above, —Z$^2$— which is as defined above, and Z$^3$ in which Z$^3$ is a trivalent or higher-valency organopolysiloxane unit, and
which may optionally be substituted by one or more hydroxyl groups and/or by —Si(OR)$_{3-a}$(R')$_a$ in which a is an integer from 0 to 2 and R and R' may be the same or different from one another and are each an organic radical,
with the proviso
that the polysiloxane compound mentioned contains at least one —Z$^1$—, —Z$^2$— or —Z$^3$— group,
that the trivalent and tetravalent Q radicals either serve to branch the main chain formed from Q and V such that the valencies which do not serve for binding in the main chain bear further branches formed from -[Q-V]— units, or the trivalent and tetravalent Q radicals are saturated by V$^3$ radicals within a linear main chain without formation of a branch,
that there is at least one group Q having at least one radical R, and
that at least one R radical in the Q groups is a polyalkylene oxide-containing organic radical R$^o$, wherein R$^o$ is a group of the formula (III)

—X-E-Y (III)

wherein X is a single bond or a divalent straight-chain, branched or cyclic hydrocarbon radical which has up to 20 carbon atoms and may optionally contain nitrogen and/or oxygen, and X is bonded to the nitrogen atom of Q via a carbon atom,
E is a group of the formula (IV)

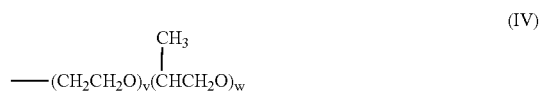

which may comprise random and blockwise sequences of the ethylene oxide and propylene oxide units and the bond to E may be via an ethylene oxide or propylene oxide unit, where
v=from 0 to 40,
w=from 0 to 40,
v+w≧1,
wherein R$^o$ is bonded to the X group via a carbon atom and to the Y group via an oxygen atom,
that the molar R$^o$:Q ratio is from 0.05 to 0.8,
wherein Y is hydrogen or a monovalent straight-chain, branched or cyclic, saturated, unsaturated or aromatic hydrocarbon radical which has up to 24 carbon atoms and may contain oxygen and/or nitrogen and/or halogen and is bonded to the E group via a carbon atom, and in which the positive charges which result from ammonium groups are neutralized by organic or inorganic acid anions.

2. A polyamino- and/or polyammonium-polysiloxane copolymer compound as claimed in claim 1, wherein V includes repeat units of the formula $V^1$ and $V^2$.

3. A polyamino- and/or polyammonium-polysiloxane copolymer compound as claimed in claim 1, wherein V includes polyalkylene oxide-containing radicals.

4. A polyamino- and/or polyammonium-polysiloxane copolymer compound as claimed in claim 1, wherein the molar ratio of the $V^1$ and $V^2$ groups is:

$V^2/V^1 > 1$.

5. A polyamino- and/or polyammonium-polysiloxane copolymer compound as claimed in claim 1, wherein the compound has an average of at least two repeat units of the formula (I).

6. A polyamino- and/or polyammonium-polysiloxane copolymer compound as claimed in claim 1, wherein the $V^1$ group is selected from divalent straight-chain, cyclic or branched, saturated, unsaturated or aromatic hydrocarbon radicals which have up to 600, preferably up to 400, carbon atoms and may optionally contain one or more groups selected from —O—, —CONH—, —CONR$^2$— in which R$^2$ is as defined above, —C(O)—, —C(S)— and —Z$^1$— in which —Z$^1$— is a group of the formula

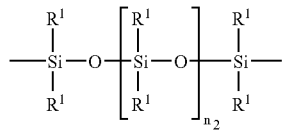

wherein
R$^1$ is C$_1$-C$_{18}$-alkyl which is optionally substituted by one or more fluorine atoms, or phenyl, and n$_2$ is as defined above.

7. The polyamino- and/or polyammonium-polysiloxane copolymer compound as claimed in claim 1, wherein the $V^1$ group is selected from:
—R$^9$— wherein R$^9$ is a divalent saturated or mono- or polyunsaturated, straight-chain or branched hydrocarbon radical having from two to 25 carbon atoms,
—(CH$_2$)$_u$C(O)O—[(CH$_2$CH$_2$O)$_q$—(CH$_2$CH(CH$_3$)O)$_r$]—C(O)(CH$_2$)$_u$
—(CH$_2$)$_u$C(O)O—R$^9$—O—C(O)(CH$_2$)$_u$— in which R$^9$ is as defined
—(CH$_2$)$_u$—R$^{10}$—(CH$_2$)$_u$— in which R$^{10}$ is an aromatic
—[CH$_2$CH$_2$O]$_q$—[CH$_2$CH(CH$_3$)O]$_r$—CH$_2$CH$_2$—,
—CH(CH$_3$)CH$_2$O[CH$_2$CH$_2$O]$_q$—[CH$_2$CH(CH$_3$)O]$_r$CH$_2$CH(CH$_3$)—
—CH$_2$CH(OH)CH$_2$—,
—CH$_2$CH(OH)(CH$_2$)$_2$CH(OH)CH$_2$—,
—CH$_2$CH(OH)CH$_2$OCH$_2$CH(OH)CH$_2$OCH$_2$CH(OH)CH$_2$—, and
—CH$_2$CH(OH)CH$_2$O—[CH$_2$CH$_2$O]$_q$—[CH$_2$CH(CH$_3$)O]$_r$—CH$_2$CH(OH)CH$_2$—
wherein
u is from 1 to 3,
q and r are from 0 to 40, and
q+r>0.

8. A process for preparing the polyamino- and/or polyammonium-polysiloxane copolymer compounds as claimed in claim 1, wherein
a) a primary amine which contains a polyalkylene oxide group and optionally further amine compounds are reacted with amino-reactive polysiloxane-containing compounds and optionally further amino-reactive compounds, or
b) the amino group of a polyamino-polysiloxane copolymer compound is alkylated with an alkylating agent which contains a polyalkylene oxide group.

9. A process of fiber treatment or fiber finishing comprising applying the polyamino- and/or polyammonium-polysiloxane copolymer compounds of claim 1 to fibers.

10. A process for initial finishing and treatment of textiles and other fibrous materials comprising applying the polyamino- and/or polyammonium-polysiloxane copolymer compounds of claim 1 to textiles or fibrous materials.

11. A process of treatment of textiles and other fibrous materials comprising applying the polyamino- and/or polyammonium-polysiloxane copolymer compounds of claim 1 to at least one of textiles, other natural and synthetic fibrous materials.

12. A fabric softener or ironing aid comprising the polyamino- and/or polyammonium-polysiloxane copolymer compounds of claim 1.

13. A process for treatment and finishing of hard surfaces comprising applying the polyamino- and/or polyammonium-polysiloxane copolymer compounds of claim 1 to a hard surface.

14. A hair or skin cosmetic system comprising the polyamino- and/or polyammonium-polysiloxane copolymer compounds of claim 1.

15. An aqueous emulsion comprising at least one polyamino- and/or polyammonium-polysiloxane copolymer compound as claimed in claim 1 and optionally one or more surfactants and optionally one or more nitrogen-free polysiloxane compounds.

16. A process of fiber finishing or treatment comprising applying the aqueous emulsion as claimed in claim 15 to a fiber.

* * * * *